US011283245B2

(12) United States Patent
Waddell

(10) Patent No.: US 11,283,245 B2
(45) Date of Patent: Mar. 22, 2022

(54) MODULAR ION GENERATOR DEVICE

(71) Applicant: Global Plasma Solutions, Inc., Charlotte, NC (US)

(72) Inventor: Charles Houston Waddell, Roanoke, VA (US)

(73) Assignee: Global Plasma Solutions, Inc., Savannah, GA (US)

(*) Notice: Subject to any disclaimer, the term of this patent is extended or adjusted under 35 U.S.C. 154(b) by 0 days.

(21) Appl. No.: 16/751,717

(22) Filed: Jan. 24, 2020

(65) Prior Publication Data

US 2020/0161839 A1 May 21, 2020

Related U.S. Application Data

(63) Continuation-in-part of application No. 16/003,327, filed on Jun. 8, 2018, now Pat. No. 10,566,769, which is a continuation of application No. 15/670,219, filed on Aug. 7, 2017, now Pat. No. 10,020,180.

(60) Provisional application No. 62/372,053, filed on Aug. 8, 2016.

(51) Int. Cl.
*A61L 9/22* (2006.01)
*H01T 23/00* (2006.01)
*F24F 3/16* (2021.01)
*F24F 8/30* (2021.01)

(52) U.S. Cl.
CPC ............ *H01T 23/00* (2013.01); *A61L 9/22* (2013.01); *F24F 3/16* (2013.01); *F24F 8/30* (2021.01)

(58) Field of Classification Search
CPC ............ H01T 23/00; A61L 9/22; F24F 8/30
See application file for complete search history.

(56) References Cited

U.S. PATENT DOCUMENTS

| 1,811,687 | A | 6/1931 | Goldberg et al. |
| 3,624,448 | A | 11/1971 | Saurenman |
| 3,652,897 | A | 3/1972 | Iosue |
| 3,769,695 | A | 11/1973 | Price |
| 3,968,405 | A | 7/1976 | Testone |
| 4,031,599 | A | 6/1977 | Testone |
| D253,281 | S | 10/1979 | Kim |
| 4,216,518 | A | 8/1980 | Simons |

(Continued)

FOREIGN PATENT DOCUMENTS

| AU | 2014214642 A1 | 8/2015 |
| CA | 2108790 A1 | 4/1995 |

(Continued)

OTHER PUBLICATIONS

Pushpawala Buddhi, et al., "Efficiency of Ionizers in Removing Airborne Particles in Indoor Environments." Journal of Electrostatics, vol. 90, pp. 79-84, Dec. 2017.

(Continued)

*Primary Examiner* — Eliza W Osenbaugh-Stewart

(57) ABSTRACT

A modular ion generator device that includes a bottom portion, two opposed side portions, a front end, a back end, and a top portion. A cavity is formed within the two opposed side portions, front end, back end, and top portion. At least one electrode is positioned within the cavity, and an engagement device is engaged to the front end and/or an engagement device engaged to the back end for allowing one or more modular ion generator devices to be selectively secured to one another.

19 Claims, 7 Drawing Sheets

(56) References Cited

U.S. PATENT DOCUMENTS

| | | | |
|---|---|---|---|
| 4,263,636 A | 4/1981 | Testone | |
| 4,264,343 A | 4/1981 | Natarajan | |
| 4,284,420 A | 8/1981 | Borysiak | |
| D286,765 S | 11/1986 | Prouty et al. | |
| 4,734,580 A | 3/1988 | Rodrigo et al. | |
| 4,757,422 A | 7/1988 | Bossard et al. | |
| 4,809,127 A | 2/1989 | Steinman et al. | |
| 4,829,398 A | 5/1989 | Wilson | |
| 5,034,651 A | 7/1991 | Domschat | |
| 5,084,077 A | 1/1992 | Junker et al. | |
| D332,942 S | 2/1993 | Julien | |
| D353,575 S | 12/1994 | Macomber | |
| 5,464,754 A | 11/1995 | Dennis et al. | |
| 5,492,557 A | 2/1996 | Vanella | |
| 5,737,176 A | 4/1998 | Muz | |
| 5,741,352 A | 4/1998 | Ford et al. | |
| 5,768,087 A | 6/1998 | Vernitskiy | |
| 5,879,435 A | 3/1999 | Satyapal | |
| 5,931,989 A | 8/1999 | Knutsson | |
| 6,019,815 A | 2/2000 | Satyapal | |
| 6,118,645 A | 9/2000 | Partridge | |
| D434,523 S | 11/2000 | Ford | |
| 6,156,099 A | 12/2000 | Hironaka et al. | |
| D443,587 S | 6/2001 | Sakasegawa | |
| 6,252,756 B1 | 6/2001 | Richie, Jr | |
| 6,330,146 B1 | 12/2001 | Blitshteyn | |
| 6,350,417 B1 | 2/2002 | Lau et al. | |
| 6,417,581 B2 | 7/2002 | Hall | |
| 6,544,485 B1 | 4/2003 | Taylor | |
| D476,298 S | 6/2003 | Lee | |
| 6,576,046 B2 | 6/2003 | Prueiie | |
| 6,653,638 B2 | 11/2003 | Fujii | |
| 6,680,033 B2 | 1/2004 | Shii | |
| 6,744,617 B2 | 6/2004 | Fujii | |
| 6,791,814 B2 | 9/2004 | Dachi et al. | |
| 6,850,403 B1 | 2/2005 | Gefter et al. | |
| 6,855,190 B1 | 2/2005 | Nikkhah | |
| D533,832 S | 12/2006 | Hock | |
| 7,177,133 B2 | 2/2007 | Riskin | |
| 7,244,289 B2 | 7/2007 | Su | |
| 7,256,979 B2 | 8/2007 | Sekoguchi et al. | |
| 7,273,515 B2 | 9/2007 | Yuen | |
| 7,408,759 B2 | 8/2008 | Gefter et al. | |
| D587,198 S | 2/2009 | Nagasawa | |
| 7,492,568 B2 | 2/2009 | Takayanagi | |
| 7,497,898 B2 | 3/2009 | Sato et al. | |
| 7,639,472 B2 | 12/2009 | Sekoguchi | |
| 7,716,772 B2 | 5/2010 | Shih et al. | |
| 7,824,477 B2 | 11/2010 | Kang et al. | |
| 7,916,445 B2 | 3/2011 | Sekoguchi | |
| 7,940,509 B2 | 5/2011 | Orihara et al. | |
| 7,948,733 B2 | 5/2011 | Hashimoto | |
| 7,961,451 B2 | 6/2011 | Sekoguchi | |
| 7,969,707 B2 | 6/2011 | Riskin | |
| 7,995,321 B2 | 8/2011 | Shimada | |
| 8,043,573 B2 | 10/2011 | Darker et al. | |
| 8,053,741 B2 | 11/2011 | Sekoguchi | |
| 8,106,367 B2 | 1/2012 | Riskin | |
| 8,134,821 B2 | 3/2012 | Fukai | |
| 8,328,902 B2 | 12/2012 | Boyden et al. | |
| 8,351,168 B2 | 1/2013 | Sicard | |
| 8,425,658 B2 | 4/2013 | Lee | |
| 8,554,924 B2 | 10/2013 | Waddell et al. | |
| 8,710,456 B2 | 4/2014 | Klochkov | |
| 8,724,286 B2 | 5/2014 | Uchida et al. | |
| 8,951,024 B2 | 2/2015 | Ishii | |
| 8,957,571 B2 | 2/2015 | Riskin | |
| 9,293,895 B2 | 3/2016 | Pucciani | |
| D754,314 S | 4/2016 | Ellis et al. | |
| 9,579,664 B2 | 2/2017 | Marra | |
| 9,623,422 B2 | 4/2017 | Overdahl | |
| 9,630,185 B1 | 4/2017 | Riskin | |
| 9,630,186 B2 | 4/2017 | Back | |
| 9,646,806 B2 | 5/2017 | Jang | |
| 9,660,425 B1 | 5/2017 | Sunshine | |
| 9,661,725 B2 | 5/2017 | Gefter | |
| 9,661,727 B2 | 5/2017 | Gefter | |
| 9,847,623 B2 | 12/2017 | Sunshine | |
| 9,849,208 B2 | 12/2017 | Waddell | |
| 9,859,090 B2 | 1/2018 | Gefter | |
| 9,948,071 B2 | 4/2018 | Chen et al. | |
| 9,985,421 B2 | 5/2018 | Sunshine | |
| 10,020,180 B2 | 7/2018 | Waddell | |
| 10,116,124 B2 | 10/2018 | Sung | |
| 10,153,623 B2 | 12/2018 | Sunshine | |
| 10,258,922 B2 | 4/2019 | Hsieh | |
| D848,945 S | 5/2019 | Lin | |
| 10,297,984 B2 | 5/2019 | Sunshine | |
| 10,322,205 B2 | 6/2019 | Waddell | |
| 10,439,370 B2 | 10/2019 | Sunshine | |
| 10,492,285 B2 | 11/2019 | Lee | |
| 10,566,769 B2 | 2/2020 | Waddell | |
| 10,695,455 B2 | 6/2020 | Waddell | |
| 10,710,098 B2 | 7/2020 | Marra | |
| 10,737,279 B2 | 8/2020 | Gefter et al. | |
| 10,758,947 B2 | 9/2020 | Heymann et al. | |
| 10,786,818 B2 | 9/2020 | Galbreath et al. | |
| 2003/0072697 A1 | 4/2003 | Taylor | |
| 2003/0147783 A1 | 8/2003 | Taylor | |
| 2006/0193100 A1* | 8/2006 | Izaki | H01T 23/00 361/220 |
| 2007/0253860 A1 | 11/2007 | Schroder | |
| 2008/0130190 A1* | 6/2008 | Shimada | H01T 23/00 361/231 |
| 2008/0160904 A1 | 7/2008 | Fl et al. | |
| 2009/0052108 A1 | 2/2009 | Innami | |
| 2009/0211459 A1 | 8/2009 | Hu et al. | |
| 2010/0172808 A1 | 1/2010 | Garashi | |
| 2010/0175391 A1 | 1/2010 | Lee et al. | |
| 2010/0157503 A1 | 6/2010 | Saito | |
| 2012/0068082 A1 | 3/2012 | Noda | |
| 2012/0154973 A1 | 6/2012 | Vaynerman et al. | |
| 2014/0076162 A1 | 3/2014 | Waddell et al. | |
| 2014/0078639 A1 | 3/2014 | Waddell et al. | |
| 2014/0103793 A1 | 4/2014 | Nishida et al. | |
| 2014/0147333 A1 | 5/2014 | Morfill | |
| 2014/0233232 A1 | 8/2014 | Radermacher | |
| 2015/0255961 A1 | 9/2015 | Chen et al. | |
| 2016/0167059 A1 | 6/2016 | Waddell | |
| 2016/0175852 A1 | 6/2016 | Waddell | |
| 2017/0040149 A1 | 2/2017 | Waddell | |
| 2017/0232131 A1 | 8/2017 | Waddell | |
| 2017/0274113 A1* | 9/2017 | Takasahara | A61L 9/22 |
| 2018/0040466 A1 | 2/2018 | Waddell | |
| 2018/0071426 A1 | 3/2018 | Waddell | |
| 2018/0169711 A1 | 6/2018 | Waddell | |
| 2019/0353359 A1 | 11/2019 | Seibold | |
| 2020/0388994 A1 | 12/2020 | Waddell | |

FOREIGN PATENT DOCUMENTS

| | | |
|---|---|---|
| CN | 107138028 A | 9/2017 |
| CN | 111228535 A | 6/2020 |
| DE | 3735219 A1 | 4/1989 |
| DE | 10355834 A1 | 7/2005 |
| DE | 202006006549 U1 | 8/2007 |
| DE | 102009035066 A1 | 3/2010 |
| DE | 102008062415 A1 | 7/2010 |
| DE | 202020102021 U1 | 4/2020 |
| EP | 0919287 A2 | 6/1999 |
| EP | 1878506 A2 | 1/2008 |
| EP | 2336665 A1 | 6/2011 |
| EP | 2683042 A2 | 1/2014 |
| EP | 2411058 B1 | 5/2015 |
| EP | 2905036 A1 | 8/2015 |
| EP | 3093564 A1 | 11/2016 |
| EP | 3165833 A1 | 5/2017 |
| EP | 3346560 A1 | 7/2018 |
| FR | 1494344 A | 9/1967 |
| GB | 1356211 A | 6/1974 |
| GB | 2117676 A | 10/1983 |
| GB | 2117676 A1 | 10/1983 |
| GB | 2245200 A | 1/1992 |
| GB | 2301179 A | 11/1996 |

(56) References Cited

FOREIGN PATENT DOCUMENTS

| | | | |
|---|---|---|---|
| GB | 2377660 | A | 1/2003 |
| GB | 2415774 | A | 1/2006 |
| GB | 2525280 | A | 10/2015 |
| GB | 2529173 | A | 2/2016 |
| ID | D0000005939-0001 | | 4/2004 |
| JP | 2681623 | B2 | 11/1997 |
| JP | 2002-043092 | A | 2/2002 |
| JP | 2004-006152 | A | 1/2004 |
| JP | 2009043580 | A | 2/2009 |
| JP | 4778289 | B2 | 9/2011 |
| JP | 5094492 | B2 | 12/2012 |
| JP | 2017-098139 | A | 6/2017 |
| KR | 10-0776572 | B1 | 11/2007 |
| KR | 10-1589055 | B1 | 1/2016 |
| KR | 2016-0138931 | A | 12/2016 |
| KR | 101800326 | B1 | 12/2017 |
| KR | 10-1816255 | B1 | 1/2018 |
| WO | WO 87/00089 | A1 | 1/1987 |
| WO | WO 98/20288 | A1 | 5/1998 |
| WO | 2006039147 | A2 | 4/2006 |
| WO | 2007009336 | A1 | 1/2007 |
| WO | WO 2007/131981 | A1 | 11/2007 |
| WO | 2010074654 | A1 | 7/2010 |
| WO | 2011136735 | A1 | 11/2011 |
| WO | WO 2012/176099 | A1 | 12/2012 |
| WO | WO 2013/173528 | A1 | 11/2013 |
| WO | 2014047445 | A1 | 3/2014 |
| WO | WO 2015/052557 | A1 | 4/2015 |
| WO | WO 2015/101348 | A1 | 7/2015 |
| WO | WO 2015/111853 | A1 | 7/2015 |
| WO | 2015138802 | A1 | 9/2015 |
| WO | 2016000411 | A1 | 1/2016 |
| WO | WO 2016/082730 | A1 | 6/2016 |
| WO | 2016134204 | A1 | 8/2016 |
| WO | WO 2016/147127 | A1 | 9/2016 |
| WO | 2016204688 | A1 | 12/2016 |
| WO | 2017022255 | A1 | 2/2017 |
| WO | WO 2017/067341 | A1 | 4/2017 |
| WO | 2017085954 | A1 | 5/2017 |
| WO | 2017152693 | A1 | 9/2017 |
| WO | 2017155458 | A1 | 9/2017 |
| WO | WO 2017/155458 | A1 | 9/2017 |
| WO | 2017168800 | A1 | 10/2017 |
| WO | WO 2017/168800 | A1 | 10/2017 |
| WO | WO 2018/175828 | A1 | 9/2018 |
| WO | WO 2018/189924 | A1 | 10/2018 |
| WO | 2018234633 | A1 | 12/2018 |
| WO | WO 2019/000694 | A1 | 1/2019 |
| WO | 2019108898 | A1 | 6/2019 |
| WO | WO 2020/037851 | A1 | 2/2020 |
| WO | WO 2020/056855 | A1 | 3/2020 |
| WO | WO 2020/078284 | A1 | 4/2020 |
| WO | 2020158967 | A1 | 8/2020 |
| WO | 2020186576 | A1 | 9/2020 |
| WO | 2020218247 | A1 | 10/2020 |
| WO | WO 2020/218247 | A1 | 10/2020 |

OTHER PUBLICATIONS

Wang, Wei, et al., "Assessment of Indoor Air Quality Using Different Air-Condition for Cooling." Advanced Materials Research, vol. 518-523, pp. 910-913, May 2012.

Wang, Yun Han, et al., "Research Progress of Air Purifier Principles and Material Technologies." Advanced Materials Research, vol. 1092-1093, pp. 1025-1028, Mar. 2015.

K. Nishikawa and H. Nojima, "Air purification technology by means of cluster ions generated by discharge plasma at atmospheric pressure." The 30th International Conference on Plasma Science, 2003. ICOPS 2003. IEEE Conference Record—Abstracts, p. 379-, 2003.

Airmaid by Interzon product brochure; Sep. 2016; Interzon AB,Propellervagen 4A,SE-183 62 Taby, Sweden www.airmaid.com.

"Products" Web Page, http://www.gpshvac.com/index.php?option=com_content&view=article&id=11&itemid=93, 1 Page, Apr. 29, 2013, retrieved from Internet Archive Wayback Machine, https://web.archive.org/web/20130429232411/http://www.gpshvac.com/index.php?option=com_content&view=article&id=11&1temid=93 on Jan. 20, 2017.

"RGF Environmental Air Purification Technologies—Guardian Air HVAC Cell" Web Page, http://www.airstarsolutions.com/Pages/RGFguardian.aspx, 3 pages, Aug. 20, 2012, retrieved from Internet Archive Wayback Machine, https://web.archive.org/web/20120820000149/http://www.airstarsolutions.com/Pages/RGFguardian.aspx on Jan. 20, 2017.

Extended European Search Report dated Sep. 28, 2021, in European Application No. 19750315.4, 60 pages.

Global Plasma Solutions. Link: https://gpshvac.com/wp-content/uploads/2017/07/GPS-FC48-AC-IOM-Rev-.pdf Visited Jul. 5, 2019. GPS-FC48-AC-IOM-Rev Self-Cleaning Ion Generator Device. (Year: 2019).

* cited by examiner

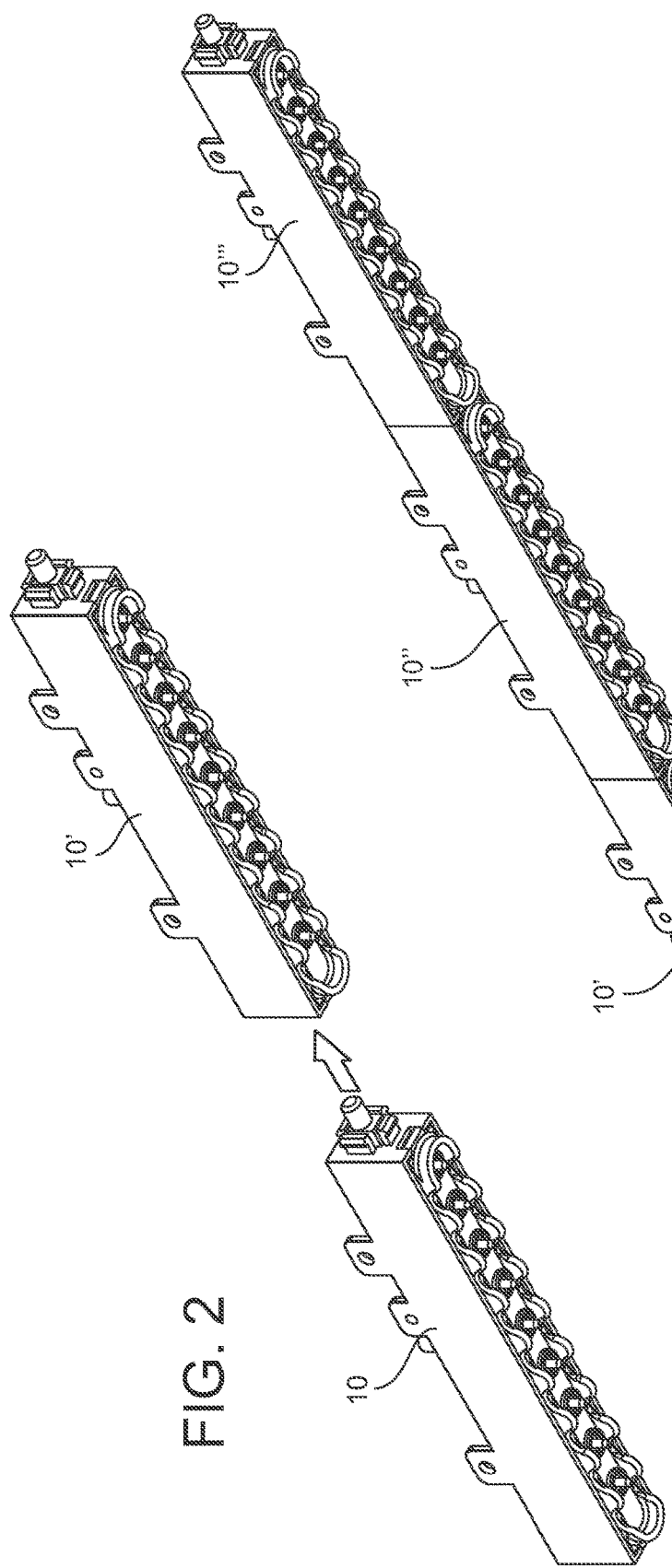
FIG. 2
FIG. 3

MODULAR ION GENERATOR DEVICE

CROSS REFERENCE TO RELATED PATENT APPLICATION

This application is a continuation-in-part of U.S. patent application Ser. No. 16/003,327 filed Jun. 8, 2018 and entitled "MODULAR ION GENERATOR DEVICE," which is a continuation of U.S. patent application Ser. No. 15/670,219 filed Aug. 7, 2017 and entitled "MODULAR ION GENERATOR DEVICE" which claims the benefit of U.S. Provisional Patent Application No. 62/372,053, filed on Aug. 8, 2016, and entitled "MODULAR ION GENERATION DEVICE," the contents of which are incorporated in full by reference herein.

FIELD OF THE INVENTION

The present invention relates generally to an ion generator device, and more generally relates to a modular ion generator device that may be selectively secured to at least one other modular ion generator device and mounted to a number of locations on a cooling coil frame or elsewhere in the HVAC system.

BACKGROUND OF THE INVENTION

Air and other fluids are commonly treated and delivered for a variety of applications. For example, in heating, ventilation and air-conditioning (HVAC) applications, air may be heated, cooled, humidified, dehumidified, filtered or otherwise treated for delivery into residential, commercial or other spaces.

Needs exist for improved systems and methods of treating and delivering air for these and other applications. It is to the provision of improved systems and methods meeting these needs that the present invention is primarily directed.

Historically ionization bars have been custom manufactured for a specific application length, thus requiring a lead-time for manufacturing. The present invention solves the custom manufacturing lead-time issue by providing a standard size off-the-shelf modular bar at a fixed length that can be connected in any quantity for the length required for the given application.

BRIEF SUMMARY OF THE INVENTION

According to an embodiment of the present invention an ion generator device that includes a bottom portion, two opposed side portions, a front end, a back end, and a top portion. A cavity is formed within the two opposed side portions, front end, and back end. At least one electrode is positioned within the cavity, and an engagement device is engaged to the front end and a receptacle within the back end allowing one or more modular ion generator devices to be selectively secured to each other.

According to another embodiment of the present invention, the ion generator device wherein one or more modular ion generator devices are selectively secured to one another.

According to yet another embodiment of the present invention, the modular ion generator device includes a magnet positioned on the device for selectively securing the device to a cooling coil frame.

According to yet another embodiment of the present invention, the modular ion generator device includes at least one flange extending from the device for engaging a magnet thereto.

According to yet another embodiment of the present invention, the modular ion generator device includes a printed circuit board housed within the cavity and the at least one electrode that extends outwardly from the printed circuit board.

According to yet another embodiment of the present invention, the modular ion generator device includes an electrode constructed of carbon fiber brushes.

According to yet another embodiment of the present invention, the modular ion generator device includes a nipple extending upwardly from the top portion of the device.

According to yet another embodiment of the present invention, the modular ion generator device includes a bottom portion that extends to an outer edge, two opposed side portions that extend upward from the outer edge, a front end that extends upward from the outer edge, a back end that extends upward from the outer edge, and a top portion. A cavity is formed within the two opposed side portions, front end, and a back end. At least one bore is disposed on the top portion, and at least one electrode is positioned within the cavity and adjacent the bore. An engagement device is engaged to the front end and a receptacle within the back end for allowing one or more ion generator devices to be selectively secured to each other.

According to yet another embodiment of the present invention, the modular ion generator device includes a power head engaged to the engagement device of the modular ion generator device.

According to yet another embodiment of the present invention, the modular ion generator device includes a cylindrical outer portion, a front end, a back end, and an area for the emitters to be exposed to the airstream. A cavity is formed within the cylindrical outer wall, front end, back end, and ionizing portion. At least one electrode is positioned within the cavity, and an engagement device is engaged to the front end and a receptacle is engaged to the back end for allowing one or more ion generator devices to be secured together.

BRIEF DESCRIPTION OF THE DRAWINGS

The present invention is illustrated and described herein with reference to the various drawings, in which like reference numbers denote like method steps and/or system components, respectively, and in which:

FIG. 2 is a top perspective view of the modular ion generator device engaged to a second ion generator device;

FIG. 3 is a top perspective view of a plurality of modular ion generator devices selectively secured to each other;

DETAILED DESCRIPTION OF THE INVENTION

Figure 1:
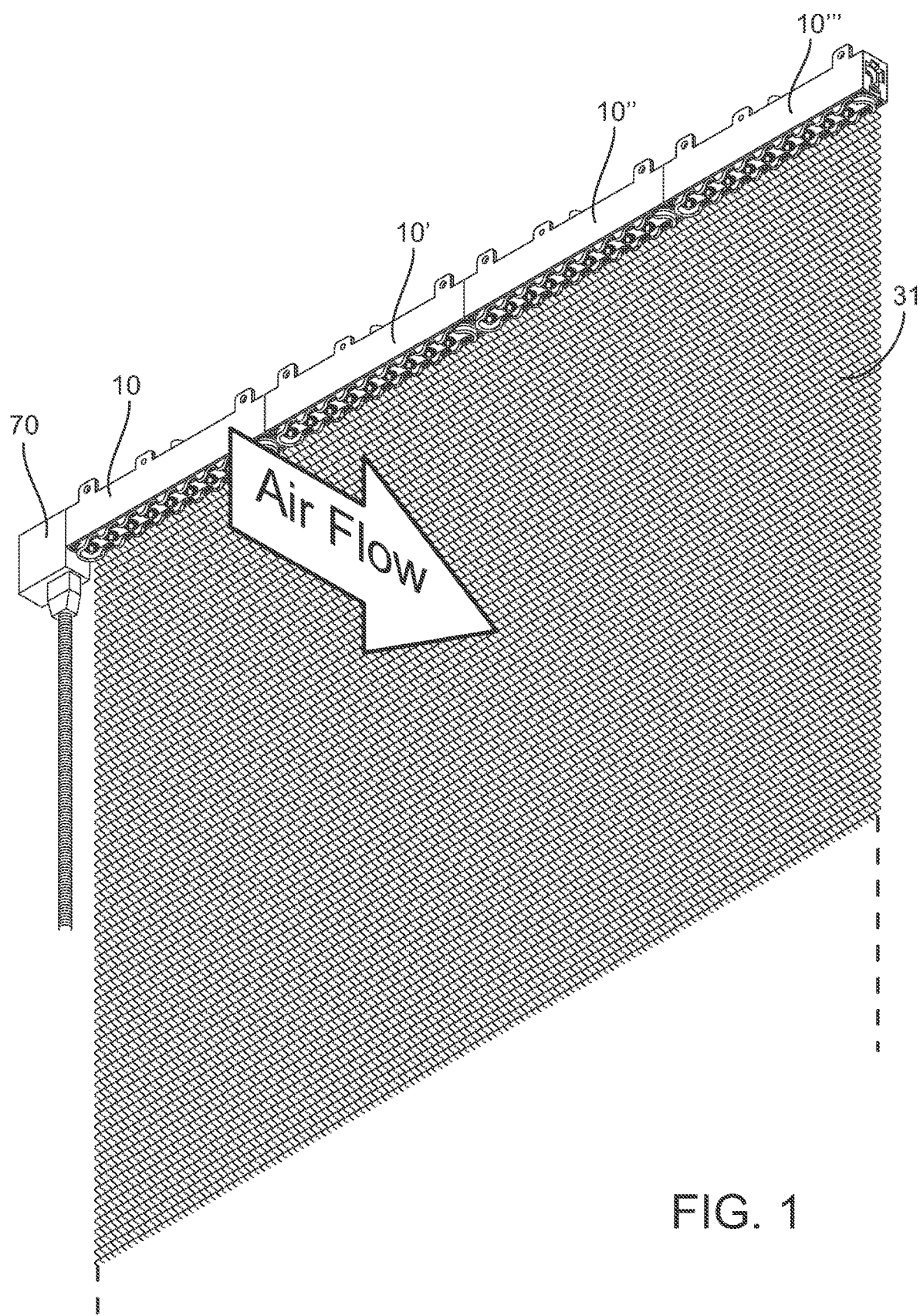
FIG. 1 is a perspective view of a plurality of modular ion generator devices engaged to each other above a coiling coil.

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Any and all patents and other publications identified in this specification are incorporated by reference as though fully set forth herein.

Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

Referring now specifically to the drawings, an ion generator device is illustrated in FIGS. 1-9 and is shown generally at reference numeral 10. The device 10 includes a housing having a bottom portion 12 that extends to an outer edge and two opposed side portions 14, a front end 16, and a back end 18 extend upwardly from the outer edge of the bottom portion 12. The two opposed side portions 14, the front end 16, and the back end 18 may have an upper edge with a ridge for receiving a top portion 20. Alternatively, the top portion 20 may be engaged to the upper edge of the two opposed side portions 14, the front end 16, and the back end 18. A cavity 22 is formed within the bottom portion 12, two opposed side portions 14, front end 16, and back end 18.

Engagement flanges 28 are disposed on the device 10. As illustrated in FIGS. 5 and 5, at least one engagement flange 28 is disposed on each of the two opposed side portions 14. Preferably, at least two engagement flanges 28 are disposed on each of the two opposed side portions 14, and most preferably two or more engagement flanges 28 are disposed on each of the two opposed side portions 14. The flanges 28 extend away from the two opposed side portions 14 and contain a bore 27 within each flange 28 and preferably centrally located within each flange 28, extending from an exterior side to an interior side of the flange 28. As illustrated, one flange 28 may have a length less than the length of other flanges 28 on the device 10. Specifically and as shown in FIGS. 4 and 5, when the device contains three flanges 28 on each of the two opposed side portions 14, one of the flanges 28, such as the flange 28 between the two other flanges 28, may have a length less than the length of the adjacent flanges 28.

Figure 7A:
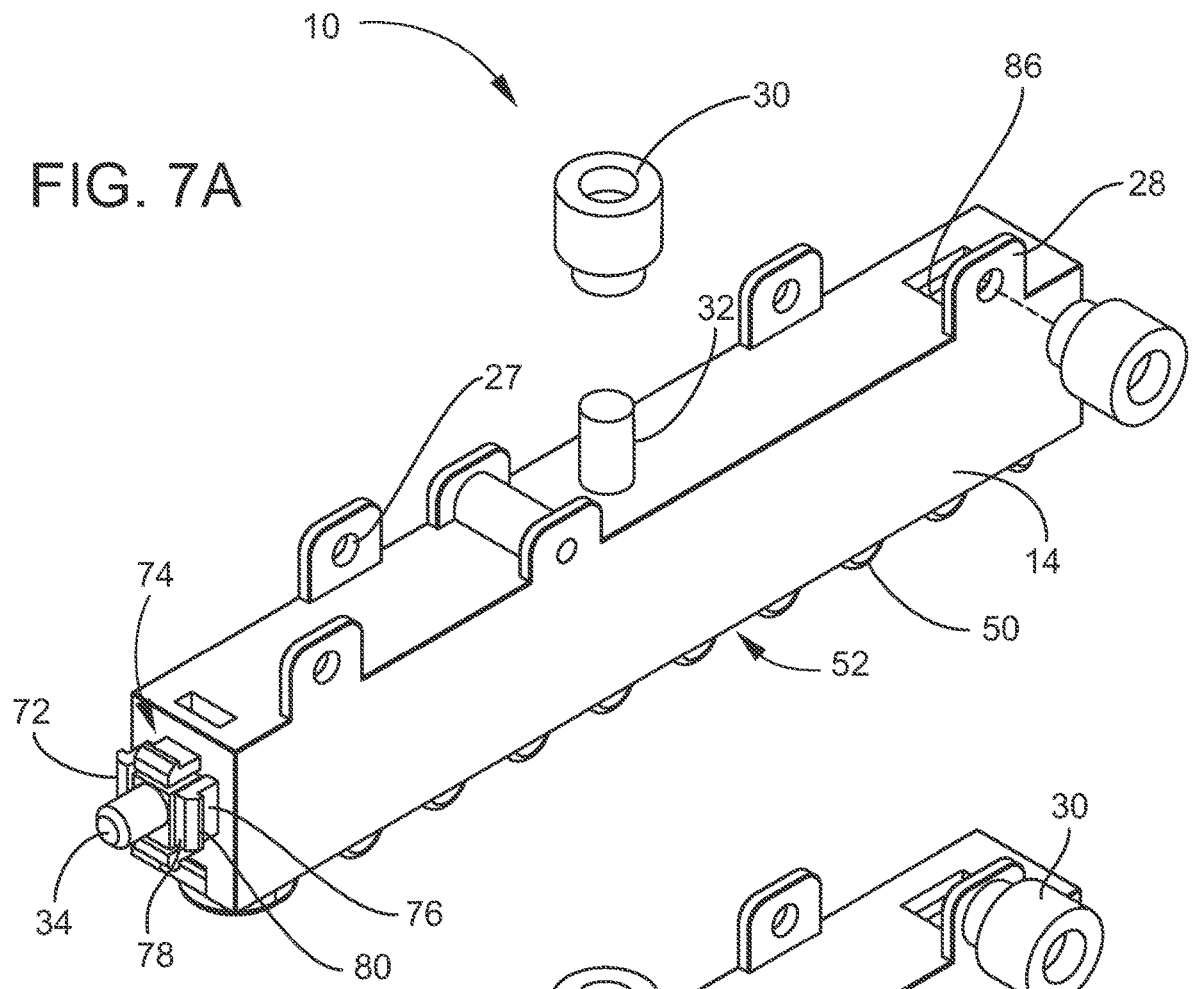
FIG. 7A is an exploded view of the modular ion generator device including magnets.
Figure 7B:
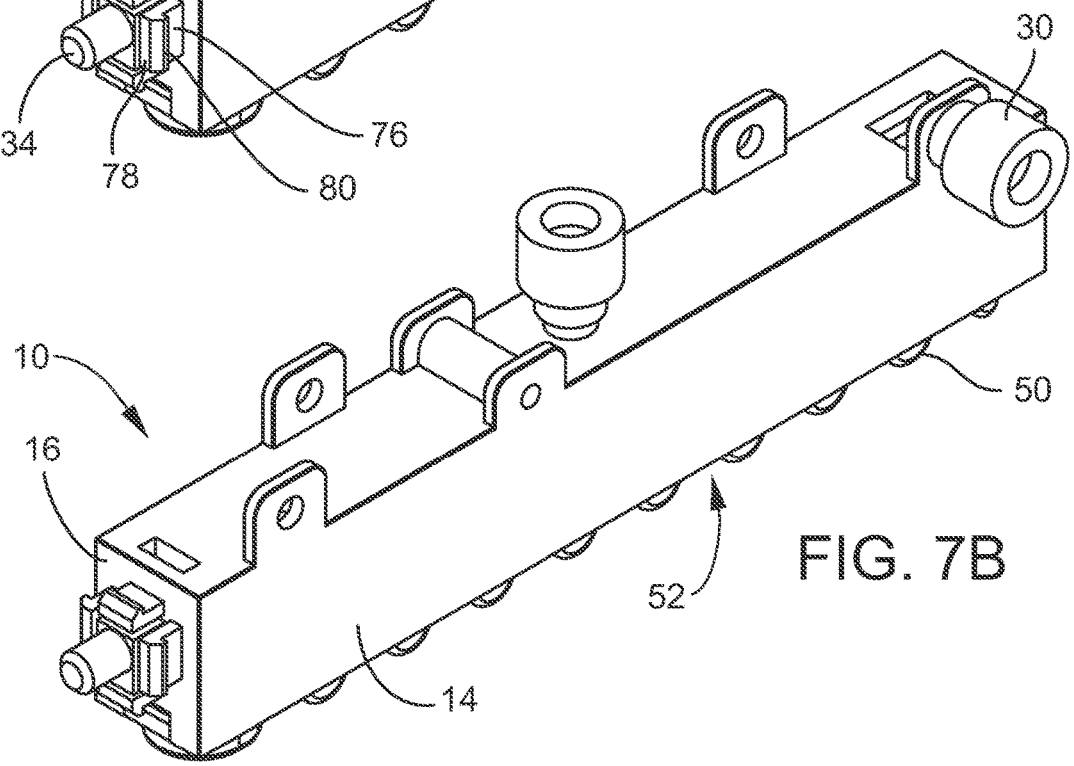
FIG. 7B is a perspective view of the modular ion generator device including magnets.

As shown in FIGS. 7A and 7B, a magnet 30 may be engaged to each flange 28. As illustrated, a circular magnet 30 may be engaged through the flange 28 with a portion of the magnet 30 extending through the bore 27 and selectively securing the magnet 30 to the flange 28. In this arrangement, the device 10 may be face mounted to a coiling coil frame 31, as illustrated in FIG. 1, or elsewhere on the HVAC system. The magnet 30 may include a post on the back side of the magnet 30 that is received within the bore 27 of each flange 28. The bottom portion 12 may also contain at least one post 32. The post 32, as shown in FIG. 7A may also receive a magnet 30. In this embodiment, the post 32 contains a bore for receiving a post on the back side of the magnet 30.

Figure 4:
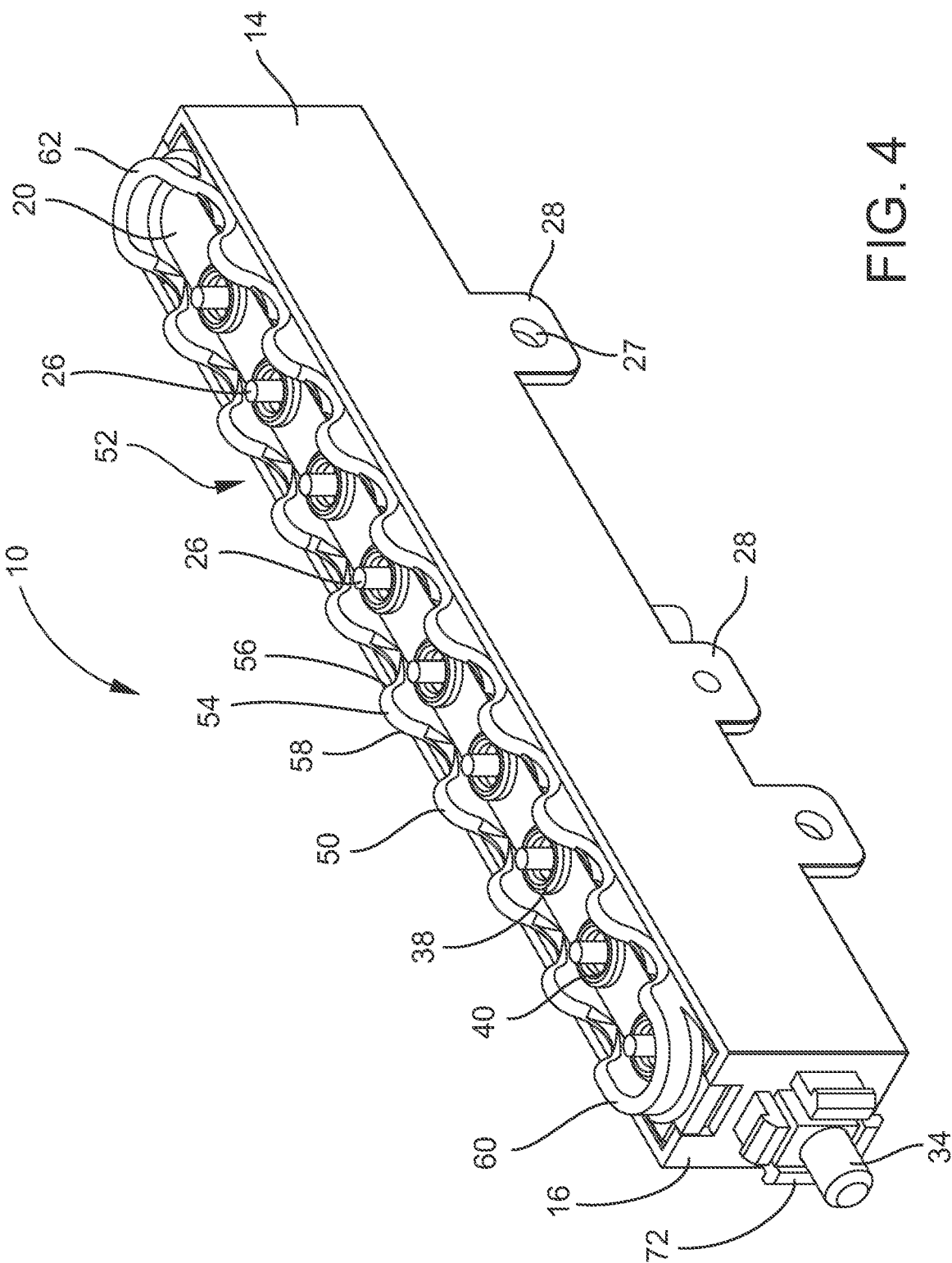
FIG. 4 is a perspective view of the modular ion generator device.
Figure 5:
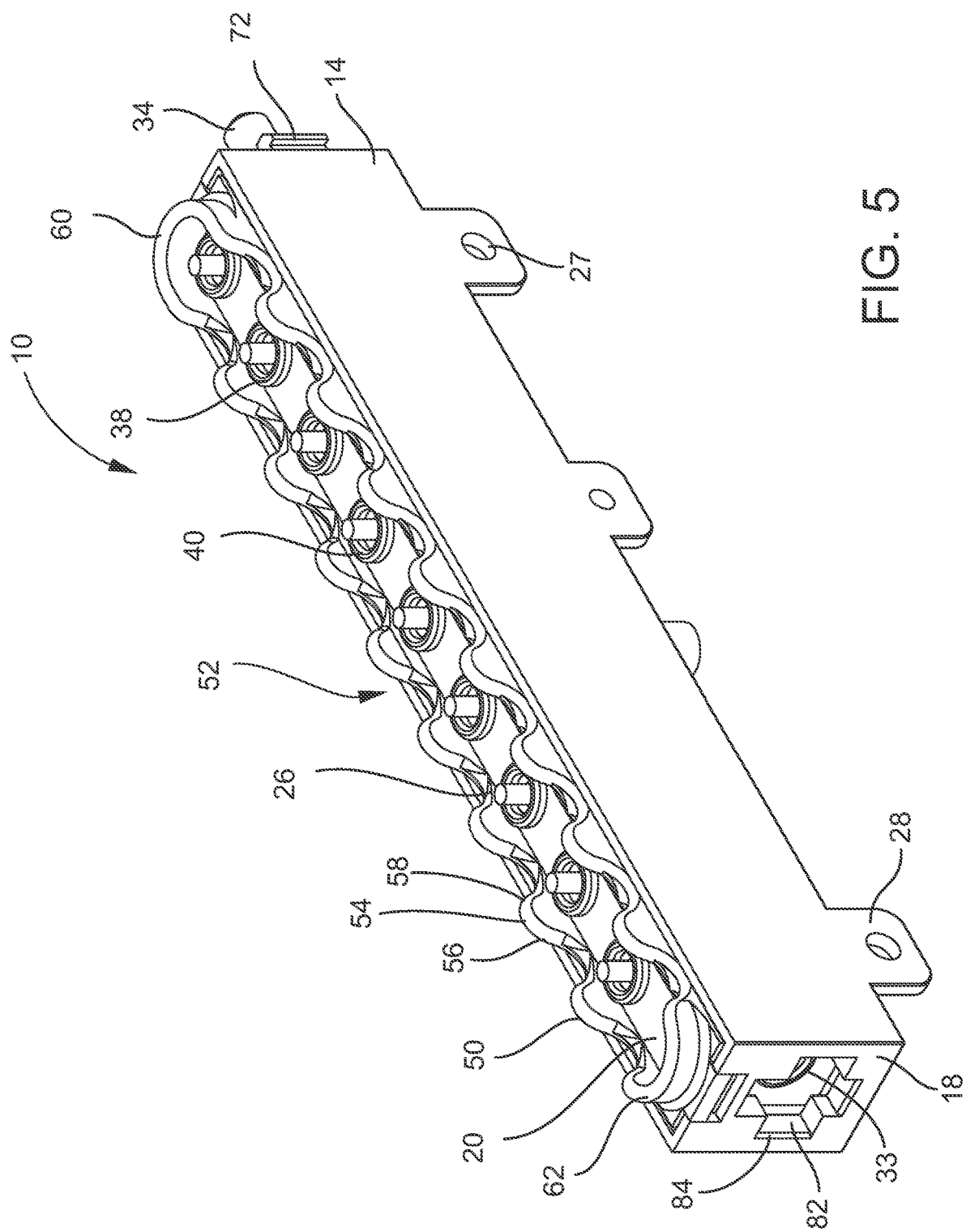
FIG. 5 is a perspective view of the modular ion generator device.

As shown in FIGS. 2, 3, and 4, the front end 16 contains a conductive device 34 that extends outward from the front end 16. The conductive device 34 is composed of brass or other conductive material and may be generally circular or have a circular cross-section. As shown in FIG. 5, the back end 18 may contain a receptacle 33, composed of brass or other conductive material that receives the conductive device 34 for selectively securing a first generator device 10 with a second generator device 10', as shown in FIG. 2. As illustrated, the conductive device 34 may be generally circular and the receptacle 33 may be correspondingly shaped or generally circular for receiving the conductive device 34. The diameter of the receptacle 33 is slightly larger than the diameter of the conductive device 34 for inserting the conductive device 34 into the receptacle 33.

At least one finger 72 is disposed adjacent the conductive device 34 on the external surface of the front end 16. As shown in FIG. 4, four fingers 72 are disposed on the external surface of the front end 16 and at various locations around the conductive device 34. In other words, a finger 72 is disposed above the conductive device 34, a finger 72 is disposed below the conductive device 34, a finger 72 is disposed on the left side of the conductive device 34, and a finger 72 is disposed on the right side of the conductive device 34. The finger 72 extends outwardly from the external face of the front end 16 and contains a retention edge 74, as shown in FIG. 7A. The finger 72 consists of an elongate portion 76 that extends outwardly from the external surface of the front end 16 and an upper portion 78 that extends perpendicularly from the elongate portion 76. A lip 80 extends downwardly from the upper portion 78 and a retention edge 74 is formed within the internal surfaces of the lip 80, upper portion 78, elongate portion 76. The upper portion 78 extends away from the conductive device 34.

Figure 6:
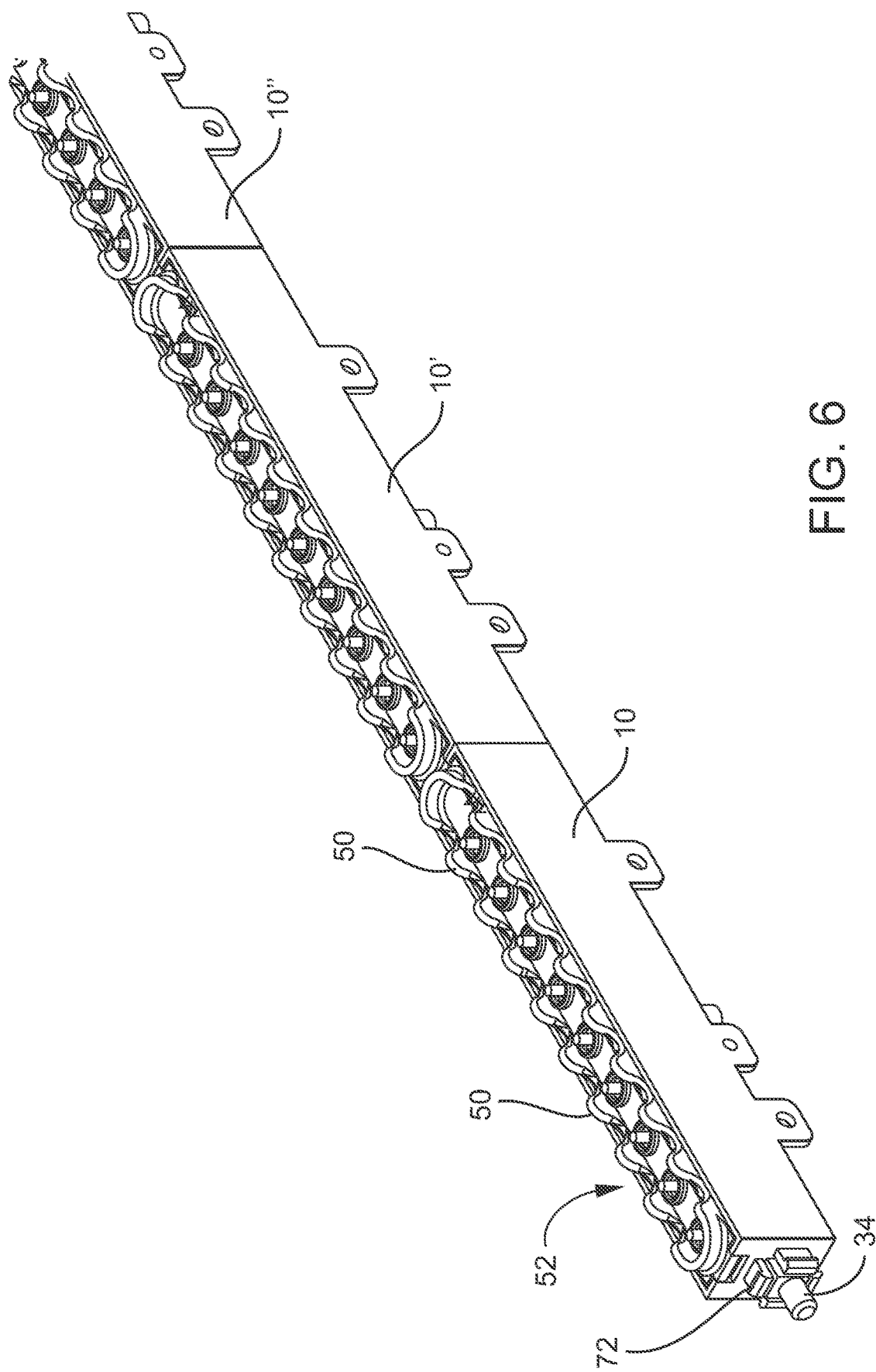
FIG. 6 is a perspective view of a plurality of modular ion generator devices engaged to each other.

The back end 18 contains a depression 82. The depression 82 contains a base portion and sides extending upwards from the base portion. Preferably, the depression 82 is formed within the back end 18. The receptacle 33 is disposed within the base portion of the depression 82. As illustrated in FIG. 5, the depression 82 may have a plus-sign shape or an X-shape depending upon the orientation of the device 10 when viewed. In other words, the depression 82 contains a central portion and four outwardly extending coves disposed on each side of the central portion of the depression 82. The upper portion of the sides of the depression 82 contains a ridge 84. When the conductive device 34 is inserted into the receptacle 33 within the depression 82, each finger 72 is also inserted into the depression 82 and the lip 80 of the finger 72 engages the ridge 84 of the side of the depression 82. In other words, the ridge 84 is retained within the retention edge 74 of the fingers 72 engaging a first device 10 to a second device 10'. As shown in FIGS. 5 and 6, a third device 10" can be engaged to the second device 10' and a fourth device 10''' can be engaged to the third device 10".

The conductive device 34 may be retained within the receptacle 33 by friction fit, or alternatively, the conductive device 34 may be magnetized, allowing the conductive device 34 to be selectively secured within the receptacle 33 or an end of the adjacent device 10. A cap may be disposed within the receptacle 33 if no ionization device will be inserted into the receptacle 33.

The receptacle 33 may be internally threaded and the conductive device 34 may be externally threaded, wherein the externally threaded conductive device 34 may be engaged or selectively secured to the internally threaded receptacle 33.

The top portion 20 of the device 10 contains at least one nipple 38 that extends upwards from the top portion 20 and contains an opening 40 that extends from the upper most surface of the nipple 38 to the cavity 22 of the device 10. The device 10 may contain two or more nipples 38 or a plurality of nipples 38. The electrode 26 is positioned adjacent the nipple 38. For example, the electrode 26 may be positioned in the cavity 22 and below the upper most surface of the nipple 38. Alternatively, the electrode 26 may extend through the hollow central portion and above the opening within the upper most surface of the nipple 38. In another embodiment, the electrode 26 may be positioned entirely within the cavity 22, allowing the electrodes 26 to proceed through the opening 40 of the nipple 38 and exiting the nipple 38. The nipples 38 are preferably centrally positioned and spaced-apart along the length of the top portion 20. The nipples 38 are preferably disposed in a straight line along the length of the top portion 20.

Alternatively, the device 10 contains a plurality of openings 40 centrally positioned and spaced-apart along the length of the top portion 20 and without a nipple 38. The openings 40 extend from the external surface of the top portion 20 to the internal surface of the top portion 20. The openings 40 are disposed in a straight line along the length of the top portion 20. The device 10 may contain one opening 40, two or more openings 40, or a plurality of openings 40. An electrode 26 is positioned adjacent the opening 40 for allowing ions to be emitted through the opening 40. Alternatively, the electrode 26 may extend through the opening 40 for emitting ions.

Figure 8:
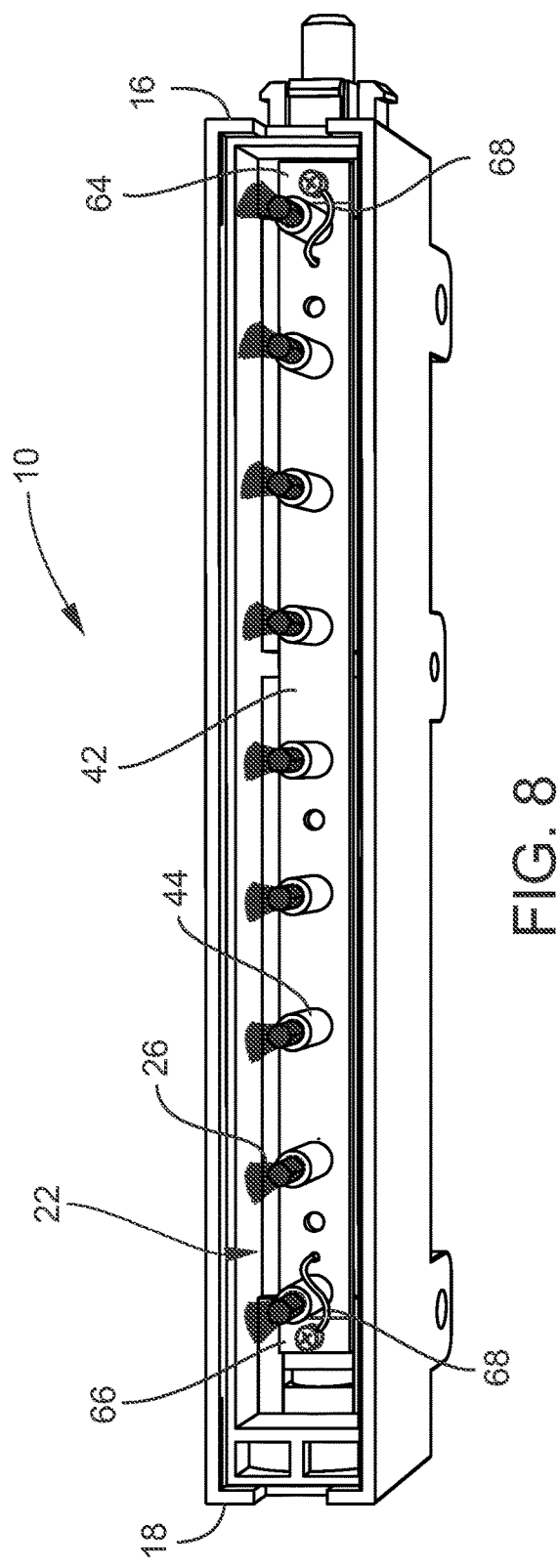
FIG. 8 is a top view of the modular ion generator device.
Figure 9:
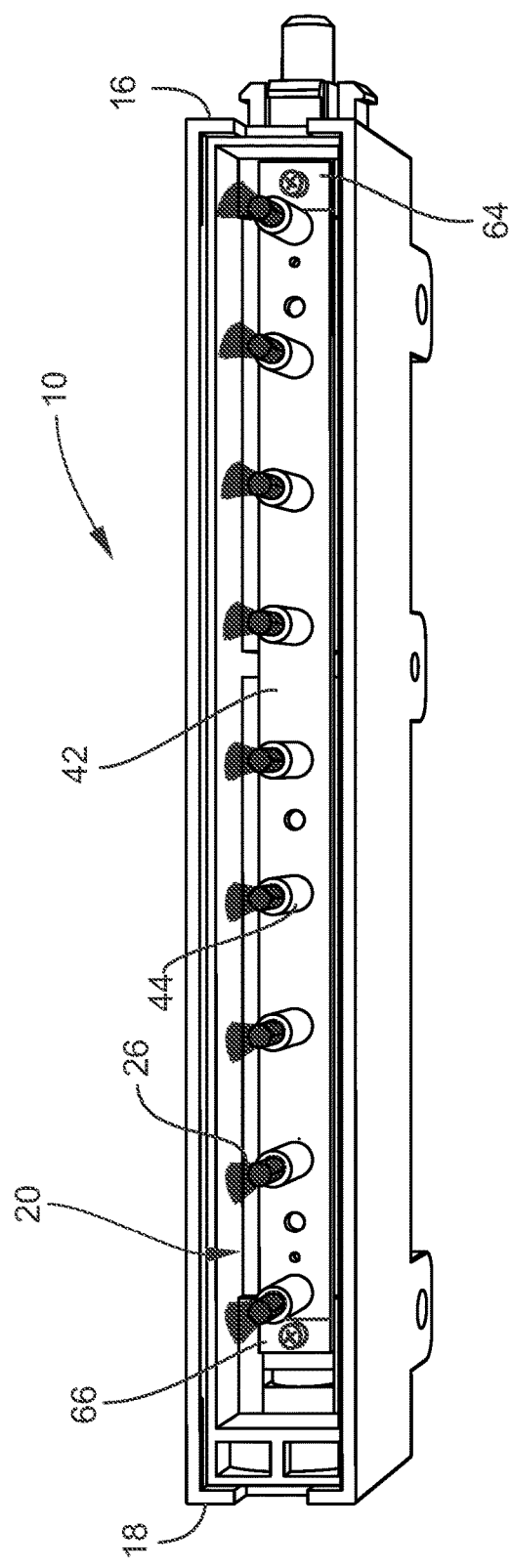
FIG. 9 is a top view of an alternative embodiment of the ion modular generator device.

Each device 10 contains at least one electrode 26, two or more electrodes 26, or a plurality of electrodes 26, as shown in FIGS. 8 and 9. The electrodes 26 are engaged or connected to a printed circuit board 42 housed within the cavity 22 of the device 10. The printed circuit board 42 generally extends along the length of the device 10 and between the front end 16 and the back end 18 of the device 10. The printed circuit board 42 allows electricity to flow along the length of the device 10 and within the cavity 22 of the device 10. The electrodes 26 may extend upwardly from the printed circuit board 42 or coupled to the printed circuit board 42 by a wire, connector, or other electrical conducting device that allows electrical current to flow from the printed circuit board 42 to the electrodes 26.

Electrical current flows along the length of the printed circuit board 42, allowing a portion of the electrical current to flow from the circuit board 42 and through the electrodes 26, if the electrodes 26 are engaged to the circuit board 42, allowing ions to flow from the end or ends of the electrodes 26. If the electrodes 26 are electrically coupled to the circuit board 42 by a wire, connector, or other electrical conducting device, the electrical current flows through the wire, connector, or other electrical conducting device and through the electrodes 26. An epoxy may be deposited within the cavity 22 and over the printed circuit board 42. The epoxy may be inserted into the cavity 22 of the device 10 through an access opening 86 disposed on the bottom portion 12 of the device 10 that extends from the exterior surface to the interior surface of the bottom portion 12 and provides access to the cavity 22. Additionally, a sheath 44 may encompass a portion of the electrode 26. As shown in FIGS. 8 and 9, the sheath 44, completely encircles a portion of the electrode 26 and extends from the printed circuit board 42 and up a distance along the electrode 26, without enclosing the upper portion of the electrode 26.

The housing of the device 10 may contain a plurality of ridges 50 disposed on the device 10. The ridges 50 are preferably located adjacent the electrodes 26, or at least a majority of the electrodes 26. As shown in FIGS. 4 and 5, a plurality of ridges 50 are disposed on the device 10 and spaced apart from each other. The ridges 50 are preferably located on the top portion 20 of the housing of the device 10, however the ridges 50 may be located on the opposed side portions 14 or on the upper edge of the opposed side portions 14. By way of an example only, the ridges 50 may be integral with the side portions 14, engaged to the side portions 14, engaged to the upper edge of the side portions 14, integral with the upper edge of the side portions 14, integral with the top portion 20, or engaged to the top portion 20. The ridges 50 are disposed on either side of the electrodes 26, and preferably extend to a height that is above the height of the electrodes 26. The ridges 50 preferably have a width that is greater than the width of the electrodes 26. A space 52 is positioned between each ridge 50 allowing air to flow between the ridges 50. The ridges 50 are spaced-apart in both the lateral and longitudinal directions. The ridges 50 are disposed on either side of the device 10 and spaced apart from each other. The ridges 50 on opposed sides of the top portion 20 face each other and are symmetrically aligned on either side of each electrode 26, or at least most electrodes 26.

The ridges 50 are preferably parabolic shaped. In other words, the ridges 50 have an arcuate top portion 54 and a first side 56 and a second side 58. The first side 56 and the second side 58 extend downwardly and outwardly from the arcuate top portion 54 to the top portion 20, the side portion 14, or the upper ridge of the side portion 14 of the housing of the device 10. The distance between the first side 56 and the second side 58 of the portion of the ridge 50 adjacent the top portion 20 is greater than the distance between the first side 56 and the second side 58 of the ridge 50 adjacent the arcuate top portion 54. In other words, the width of the ridge 50 increases as it extends downward from the arcuate top portion 54. The ridges 50 may also be another shape sufficient for the purposes of the invention, such as square, triangle, rectangular or other geometric shape.

At the front end 16 and back end 18 of the housing of the device 10, a first extension 60 and a second extension 62 extend upwards from the device, and as illustrated extend upwards from the top portion 20 of the device 10. The first extension 60 is adjacent the front end 16 and the second extension 62 is adjacent the back end 18. The first extension 60 and the second extension 62 are generally c-shaped, and as shown in FIGS. 4-5, the first extension 60 and the second extension 62 do not have to be identical. The first extension 60 may partially surround an electrode 26, while the second extension 62 may or may not partially surround an electrode 26. The first extension 60 may be positioned entirely on the top portion 20 of the housing or may be positioned on the front end 16, positioned on the front end 16 and the top portion 20, positioned on the front end 16 and opposed side portions 14, or positioned on the front end 16, opposed side portions 14, and the top portion 20. The second extension 62 may be positioned entirely on the top portion 20 of the housing or may be positioned on the back end 18, positioned on the back end 18 and the top portion 20, positioned on the back end 18 and opposed side portions 14, or positioned on the back end 18, opposed side portions 14, and the top portion 20.

The printed circuit board 42 may be engaged within the device 10 in two alternative arrangements. As illustrated in FIG. 8, a first electrical connector 64 and a second electrical connector 66 are positioned on either side of the cavity 22. The first electrical connector 64 may be positioned adjacent the internal side of the front end 16 and the second electrical connector 66 may be positioned adjacent the internal side of the back end 18. The first electrical connector 64 positioned adjacent the internal side of the front end 16 is coupled to the conductive device 34 for allowing electricity to flow from the conductive device 34 to the first electrical connector 64. The second electrical connector 66 is coupled to a conductive element within the receptacle 33 for allowing electricity to flow from the second electrical connector 66 to the receptacle and allowing the electricity to progress from the conductive element within the receptacle 33 to an conductive device 34 that may be selectively secured to the receptacle 33.

The first electrical connector 64 and second electrical connector 66 each contain an eye for receiving the first end of a wire 68. The second end of the wire 68 is engaged to an end of the printed circuit board 42 and allowing electricity to flow from the first electrical connector 64 through the wire 68 to the first end of the printed circuit board 42. The electricity flow through the printed circuit board 42, allowing a portion of the electricity to flow through the electrodes 26 and producing ions, wherein the remainder of the electricity progresses down the printed circuit board 42 towards the second end. The remainder of the electricity flows to the second end of the printed circuit board 42 and through the wire 68 to the second electrical connector 66. A screw or other fastener may be used to engage the first electrical connector 64, a second electrical connector 66, and printed circuit board 42 to the device 10.

Alternatively, as shown in FIG. 9, the first end of the printed circuit board 42 is engaged to the first electrical connector 64 and the second end of the printed circuit board 42 is engaged to the second electrical connector 66. The first electrical connector 64 and first end of the printed circuit board 42 each contain a hole, and the hole in the printed circuit board 42 is placed overtop the hole in the first electrical connector 64. A fastener, such as a screw, is inserted in the hole, allowing electricity to flow from the first electrical connector 64 through the screw and into the printed circuit board 42. The second electrical connector 66 and second end of the printed circuit board 42 each contain a hole, and the hole in the printed circuit board 42 is placed overtop the hole in the second electrical connector 66. A fastener, such as a screw, is inserted in the hole, allowing electricity to flow from the printed circuit board 42 and into the second electrical connector 66.

The electrodes 26 may consist of a high voltage wire having a first end and a second end. The first end of the high voltage wire may contain a plurality of bristles or clusters that extend upwardly from the printed circuit board 42. The bristles are composed of any material that conducts electricity. The bristles or clusters may be composed of nylon, carbon fibers, or a thermoplastic polymer imbedded with conductive material that allows the polymer to conduct electricity. For example, the bristles may be composed of polypropylene or polyethylene and impregnated with carbon. Generally, the bristles of the electrode 26 may contain between about 20 to about 80 wt % polypropylene copolymer or polyethylene copolymer, between about 5 to about 40 wt % talc, and from about 5 to 40 wt % carbon black. However, any other resistive, inductive, reactive or conductive plastic or non-metallic material may be utilized for the bristles. As illustrated in FIG. 4, the electrode consists of a plurality of carbon fibers having a first end and a second end. The first end is engaged to the printed circuit board 42 for receiving the flow of electricity flowing through the printed circuit board 42 and the second end extends upwardly from the printed circuit board 42 for emitting ions. Each fiber within the cluster can emit ions from its second end.

The device 10 may produce approximately equal amounts of positive and negative ions, regardless of airflow velocity or other conditions such as humidity or temperature. In example forms, the device 10 produces positive ions and negative ions in a concentration of at least about 40 million ions per cubic centimeter as measured 2 inches from the device electrodes. In alternate embodiments, the device generates negative ions only, or positive ions only, or generate negative ions and positive ions in unequal quantities.

In one embodiment, the top portion 20 of the device 10 may contain an LED bore that extends through the top portion 20 and into the cavity 22. An LED light may be positioned over the LED bore and engaged to an LED wire that extends from a circuit board to the LED light. When current is flowing through the high voltage wires current also flows through the LED wire and illuminates the LED light, indicating the device 10 is operating. The top portion 20 contains a first power supply bore and a second power supply bore for receiving the positive and negative power supply wires that serve as the power supply source.

The device 10 may be positioned and secured in place within the housing of the air handler unit such that the electrodes are aligned generally perpendicularly to the direction of the airflow across the device 10, to prevent recombination of the positively charged ions with the negatively charged ions.

The treatment of air by delivery of bipolar ionization to an airflow within a conduit according to the systems and methods of the present invention may be utilized for various purposes. For example, application of bipolar ionization to an airflow within an HVAC conduit such as an air handler housing or duct may be utilized to abate allergens, pathogens, odors, gases, volatile organic compounds, bacteria, virus, mold, dander, fungus, dust mites, animal and smoke odors, and/or static electricity in a treated air space to which the airflow is directed. Ionization of air in living and working spaces may reduce building related illness and improve indoor air quality; and additionally can reduce the quantity of outside air needed to be mixed with the treated indoor air, reducing heating and cooling costs by enabling a greater degree of air recirculation.

As shown in FIG. 1, a power head 70 provides, preferably AC current, to the device 10. Alternatively, the power head 70 could provide DC current. The power head 70 contains a female portion or receptacle allowing the conductive device 34 of the device 10 to be inserted and mated to the power head 70. The power head 70 may also contain a depression, similar to the depression 82 on the back end 18 of the device 10. The depression contains a base portion and sides extending upwards from the base portion. The female portion or may be disposed within the base portion of the depression. The depression may have a plus-sign shape or an X-shape depending upon the orientation of the power head 70 when viewed. In other words, the depression contains a central portion and four coves disposed on each side of the central portion of the depression. The upper portion of the sides of the depression contain a ridge, and the lip 80 of the fingers 72 engage the ridge of the sides of the depression. In other words, the ridge is retained within the retention edge 74 of the fingers 72 engaging a device 10 to the power head 70.

In one embodiment, the female portion of the power head 70 is internally threaded for the receiving the externally threaded conductive device 34 in a selectively secured arrangement. Selectively secured means the two devices, or in this instance power head 70 and device 10, can be separated from each other.

The electrodes 26 within the ionizer may be removable or replaceable. The emitter points may be constructed of conductive resins, gold, titanium, or any other corrosion resistant conductive material.

Although the present invention has been illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present invention and are intended to be covered by the following claims.

What is claimed is:

1. An ion generator device, comprising:
    a housing;
        a cavity formed within the housing having a front end and a back end;
        a plurality of openings positioned along the housing;
        a plurality of ridges positioned adjacent the openings;
        at least one finger extending from the front end of the housing;
        at least one electrode positioned within the cavity; and
        a conductive device engaged to the front end and a receptacle within the back end for allowing one or more modular ion generator devices to be selectively secured to each other.

2. The modular ion generator device of claim 1, further comprising a magnet positioned on the device for selectively securing the device to a metal surface.

3. The modular ion generator device of claim 1, further comprising at least one flange extending from the device.

4. The modular ion generator device of claim 1, further comprising a printed circuit board housed within the cavity and the at least one electrode extends outwardly from the printed circuit board.

5. The modular ion generator device of claim 1, where the at least one electrode is constructed of carbon fiber brushes.

6. An ion generator device, comprising:
    a housing comprising a bottom portion that extends to an outer edge, two opposed side portions that extend upward from the outer edge, a front end that extends upward from the outer edge, a back end that extends upward from the outer edge, and a top portion;
        a cavity formed within the two opposed side portions, front end, and back end; a plurality of openings disposed on the top portion;
        a plurality of electrodes positioned within the cavity;
        at least one finger extending from the front end of the housing; and
        a conductive device extending from the front end and a receptacle within the back end for allowing one or more ion generator devices to be selectively secured to each other.

7. The modular ion generator device of claim 6, further comprising a power head engaged to the modular ion generator device.

8. The modular ion generator device of claim 6, further comprising a magnet positioned on the device for selectively securing the device to a metal surface.

9. The modular ion generator device of claim 6, further comprising at least one flange extending from the device for engaging a magnet thereto.

10. The modular ion generator device of claim 6, further comprising at least one nipple extending from the top portion.

11. The modular ion generator device of claim 6, where the at least one electrode may be constructed of carbon fiber brushes.

12. The ion generator device of claim 6, further comprising a plurality of ridges adjacent the electrodes.

13. The ion generator device of claim 6, wherein four fingers extend from the frontend of the housing.

14. An ion generator device, comprising:
    a housing comprising a front end and a back end; a cavity formed within the housing;
    a plurality of openings positioned along the housing; at least one finger extending from the front end;
    at least one electrode extending from the housing; and
    a conductive device engaged to the front end and a receptacle within the back end for allowing one or more modular ion generator devices to be selectively secured to each other.

15. The ion generator device of claim 14, wherein one or more modular ion generator devices are selectively engaged to one another.

16. The ion generator device of claim 14, further comprising a magnet positioned on the device for selectively securing the device to a metal surface.

17. The ion generator device of claim 14, further comprising a plurality of ridges adjacent the electrodes.

18. The ion generator device of claim 14, where the electrodes are removable.

19. The ion generator device of claim 14, where the electrodes are constructed of carbon fiber brushes.

* * * * *